US00PP21313P2

(12) United States Plant Patent
De Jong

(10) Patent No.: US PP21,313 P2
(45) Date of Patent: Sep. 21, 2010

(54) *HYPERICUM* PLANT NAMED 'KOLMAREST'

(50) Latin Name: *Hypericum×inodorum*
Varietal Denomination: Kolmarest

(75) Inventor: Jan De Jong, Heelsum (NL)

(73) Assignee: Kolster Beheer B.V., Boskoop (NL)

( * ) Notice: Subject to any disclaimer, the term of this patent is extended or adjusted under 35 U.S.C. 154(b) by 112 days.

(21) Appl. No.: 12/315,156

(22) Filed: Nov. 28, 2008

(51) Int. Cl.
*A01H 5/00* (2006.01)

(52) U.S. Cl. ..... Plt./442

(58) Field of Classification Search ..... Plt./442
See application file for complete search history.

(56) References Cited

OTHER PUBLICATIONS

Northeast nursery available at: http://www.northeastnursery.com/plants/novalis.html accessed on Mar. 29, 2010.*

* cited by examiner

*Primary Examiner*—Wendy C Haas
(74) *Attorney, Agent, or Firm*—C. A. Whealy

(57) ABSTRACT

A new and distinct cultivar of *Hypericum* plant named 'Kolmarest', characterized by its compact, upright and outwardly spreading plant habit; moderately vigorous growth habit; short internodes; small dark green-colored leaves; uniform and freely flowering habit; uniform and high density of fruits; red-colored fruits; and resistance to *Puccinia* rust.

2 Drawing Sheets

Botanical designation: *Hypericum×inodorum.*
Cultivar denomination: 'KOLMAREST'.

BACKGROUND OF THE INVENTION

The present invention relates to a new and distinct cultivar of *Hypericum* plant, botanically known as *Hypericum×inodorum* and hereinafter referred to by the name 'Kolmarest'.

The new *Hypericum* plant is a product of a planned breeding program conducted by the Inventor in Heelsum, The Netherlands. The objective of the breeding program is to create new pot-type *Hypericum* cultivars with strong foliage and numerous attractive fruits.

The new *Hypericum* plant originated from a cross-pollination in 2000 in Heelsum, The Netherlands of *Hypericum×inodorum* 'Pinky Flair', not patented, as the female, or seed parent with a proprietary selection of *Hypericum×inodorum* identified as code number H-27, not patented, as the male, or pollen, parent. The new *Hypericum* was discovered and selected by the Inventor as a single flowering plant within the progeny of the stated cross-pollination in a controlled greenhouse environment in Heelsum, The Netherlands in 2003.

Asexual reproduction of the new *Hypericum* plant by vegetative cuttings in Boskoop, The Netherlands since 2004 has shown that the unique features of this new *Hypericum* plant are stable and reproduced true to type in successive generations.

SUMMARY OF THE INVENTION

Plants of the new *Hypericum* have not been observed under all possible environmental conditions. The phenotype may vary somewhat with variations in environment such as temperature and light intensity without, however, any variance in genotype.

The following traits have been repeatedly observed and are determined to be the unique characteristics of 'Kolmarest'.

These characteristics in combination distinguish 'Kolmarest' as a new and distinct cultivar of *Hypericum:*

1. Compact, upright and outwardly spreading plant habit.
2. Moderately vigorous growth habit.
3. Short internodes.
4. Small dark green-colored leaves.
5. Uniform and freely flowering habit; uniform and high density of fruits.
6. Red-colored fruits.
7. Resistant to *Puccinia* rust.

Plants of the new *Hypericum* differ primarily from plants of the female parent, 'Pinky Flair', in the following characteristics:

1. Plants of the new *Hypericum* have smaller leaves than plants of 'Pinky Flair'.
2. Plants of the new *Hypericum* have smaller fruits than plants of 'Pinky Flair'.
3. Plants of the new *Hypericum* and 'Pinky Flair' differ in fruit color as plants of 'Pinky Flair' have orange red-colored fruits.
4. Plants of the new *Hypericum* are resistant to *Puccinia* rust whereas plants of 'Pinky Flair' are susceptible to *Puccinia* rust.

Plants of the new *Hypericum* differ from plants of the male parent selection in the following characteristics:

1. Plants of the new *Hypericum* have shorter lateral branches than plants of the male parent selection.
2. Plants of the new *Hypericum* have darker green-colored leaves than plants of the male parent selection.
3. Plants of the new *Hypericum* and the male parent selection differ in fruit color as plants of the male parent selection have salmon-colored fruits.

Plants of the new *Hypericum* can be compared to plants of the *Hypericum* 'Kolmred', disclosed in U.S. Plant Pat. No. 13,554. In side-by-side comparisons, conducted in Boskoop, The Netherlands, plants of the new *Hypericum* differed primarily from plants of 'Kolmred' in the following characteristics:

1. Plants of the new *Hypericum* had shorter lateral branches than plants of 'Kolmred'.

2. Plants of the new *Hypericum* had smaller leaves than plants of 'Kolmred'.
3. Plants of the new *Hypericum* had smaller fruits than plants of 'Kolmred'.
4. Plants of the new *Hypericum* were more resistant to *Puccinia* rust than plants of 'Pinky Flair'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Hypericum*.

The photograph on the first sheet comprises a side perspective view of a typical flowering plant of 'Kolmarest' grown in a container.

The photograph at the top of the second sheet is a close-up view of typical flowers and developing fruits of 'Kolmarese'; the photograph at the center of the second sheet is a close-up view of typical fruits of 'Kolmarest'; the photograph at the bottom of the second sheet is a close-up view of a typical leaf of 'Kolmarest'.

DETAILED BOTANICAL DESCRIPTION

Plants used for the aforementioned photographs and following description were grown for two years under conditions which closely approximate commercial *Hypericum* production conditions in containers in an outdoor nursery in Boskoop, The Netherlands. During the production of the plants, day temperatures ranged from 12° C. to 30° C. and night temperatures ranged from 4° C. to averaged 14° C. In the following description, color references are made to The Royal Horticultural Society Colour Chart, 2001 Edition, except where general terms of ordinary dictionary significance are used.

Botanical classification: *Hypericum×inodorum* 'Kolmarest'.

Parentage:

*Female, or seed, parent.*—*Hypericum×inodorum* 'Pinky Flair', not patented.

*Male, or pollen, parent.*—Proprietary selection of *Hypericum×inodorum* identified as code number H-27, not patented.

Propagation:

*Type cutting.*—Vegetative cuttings.

*Time to initiate roots.*—About three weeks at 18° C. to 30° C.

*Time to produce a rooted young plant.*—About five weeks at 18° C. to 30° C.

*Root description.*—Medium in thickness; fibrous; white in color.

*Rooting habit.*—Moderately freely branching; moderately dense.

Plant description:

*Form/growth habit.*—Perennial shrub. Compact, upright and outwardly spreading plant habit, narrow inverted triangle; moderately vigorous growth habit.

*Branching habit.*—Freely basally branching habit with about 17 lateral branches; pinching enhances lateral branch development.

*Plant height.*—About 36.4 cm.

*Plant width* (*spread*).—About 43.3 cm.

*Lateral branch description.*—Length: About 23.9 cm. Diameter: About 3 mm. Internode length: About 3 cm. Strength: Moderately strong. Texture: Smooth, glabrous. Color: Close to 145A to 145B tinged with close to 173A; older stems, close to N199C to N199D.

Foliage description:

*Arrangement.*—Opposite, simple; sessile.

*Length.*—About 5.5 cm.

*Width.*—About 3 cm.

*Shape.*—Ovate.

*Apex.*—Obtuse to retuse.

*Base.*—Obtuse.

*Margin.*—Entire.

*Texture, upper and lower surfaces.*—Smooth, glabrous; rugose.

*Venation pattern.*—Pinnate.

*Color.*—Developing leaves, upper surface: Darker than 143A. Developing leaves, lower surface: Close to 138B. Fully expanded leaves, upper surface: Between 137A and 139A; venation, close to 144B. Fully expanded leaves, lower surface: Close to 138A; venation, close to 144C.

Flower description:

*Flower arrangement and shape.*—Bright yellow-colored single flowers arranged in terminal compound umbels; freely flowering habit with about nine flowers per umbel. Flowers face mostly upright.

*Fragrance.*—None detected.

*Natural flowering season.*—From July to September in The Netherlands.

*Flower longevity.*—Flowers last about two or three days on the plant; flowers not persistent.

*Fruit longevity.*—About one month.

*Flower buds.*—Length: About 7 mm. Diameter: About 6 mm. Shape: Broadly ovate to globular. Color: Close to 12A, towards the apex, close to 17A.

*Inflorescence size.*—Height: About 5.3 cm. Diameter: About 7.6 cm.

*Flowers.*—Diameter: About 3.1 cm. Depth (height): About 1.6 cm.

*Petals.*—Quantity/arrangement: Five in a single whorl. Length: About 1.3 cm. Width: About 9 mm. Shape: Obovate. Apex: Bluntly acute. Base: Attenuate. Margin: Entire. Texture, upper and lower surfaces: Glabrous, smooth. Aspect: Concave. Color: When opening and fully opened, upper surface: Close to 13A to 13B color becoming closer to 20A with development. When opening and fully opened, lower surface: Close to 12A.

*Sepals.*—Quantity/arrangement: Five in a single whorl. Length: About 1 cm. Width: About 6 mm. Shape: Ovate to broadly ovate. Apex: Broadly acute. Base: Broadly cuneate. Margin: Entire. Texture, upper and lower surfaces: Glabrous, smooth. Color: When opening, upper surface: Close to 143B. When opening, lower surface: Close to 143C. Fully opened, upper surface: Close to 143A. Fully opened, lower surface: Close to 144A.

*Peduncles.*—Strength: Moderately strong. Length: About 1.7 cm. Diameter: About 1 mm. Texture: Smooth, glabrous. Color: Close to 177A.

*Pedicels.*—Strength: Moderately strong. Length: About 2.1 cm. Diameter: About 1 mm. Texture: Smooth, glabrous. Color: Close to 177A.

*Reproductive organs.*—Stamens: Quantity per flower: About 100. Filament length: About 1.25 mm. Filament color: Close to 12A. Anther shape: Broadly oval. Anther length: About 0.5 mm. Anther color: Close to 15A to 15B. Pollen amount: Moderate. Pollen color: Close to 17A to 17B. Pistils: Quantity per flower: Single pistil with three stigmas. Pistil length: About 3.5 mm. Stigma shape: Club-shaped. Stigma color: Close to 34B. Style length: About 3 mm. Style color: Close to 151C. Ovary color: Close to 151C.

*Fruits.*—Length: About 9 mm. Diameter: About 8 mm. Shape: Roughly spherical. Texture: Smooth, glabrous. Color: Close to 46C; towards the base, close to 49D.

*Seeds.*—Length: About 0.8 mm. Diameter: About 0.5 mm. Color: Between 199A and N199A.

Disease/pest resistance: Plants of the new *Hypericum* have been noted to be resistant to *Puccinia* rust. Plants of the new *Hypericum* have not been observed to be resistant to pests and other pathogens common to *Hypericum*.

Weather/temperature tolerance: Plants of the new *Hypericum* have been observed to tolerate wind, rain and temperatures ranging from about −20° C. to about 40° C.

It is claimed:

1. A new and distinct *Hypericum* plant named 'Kolmarest' as illustrated and described.

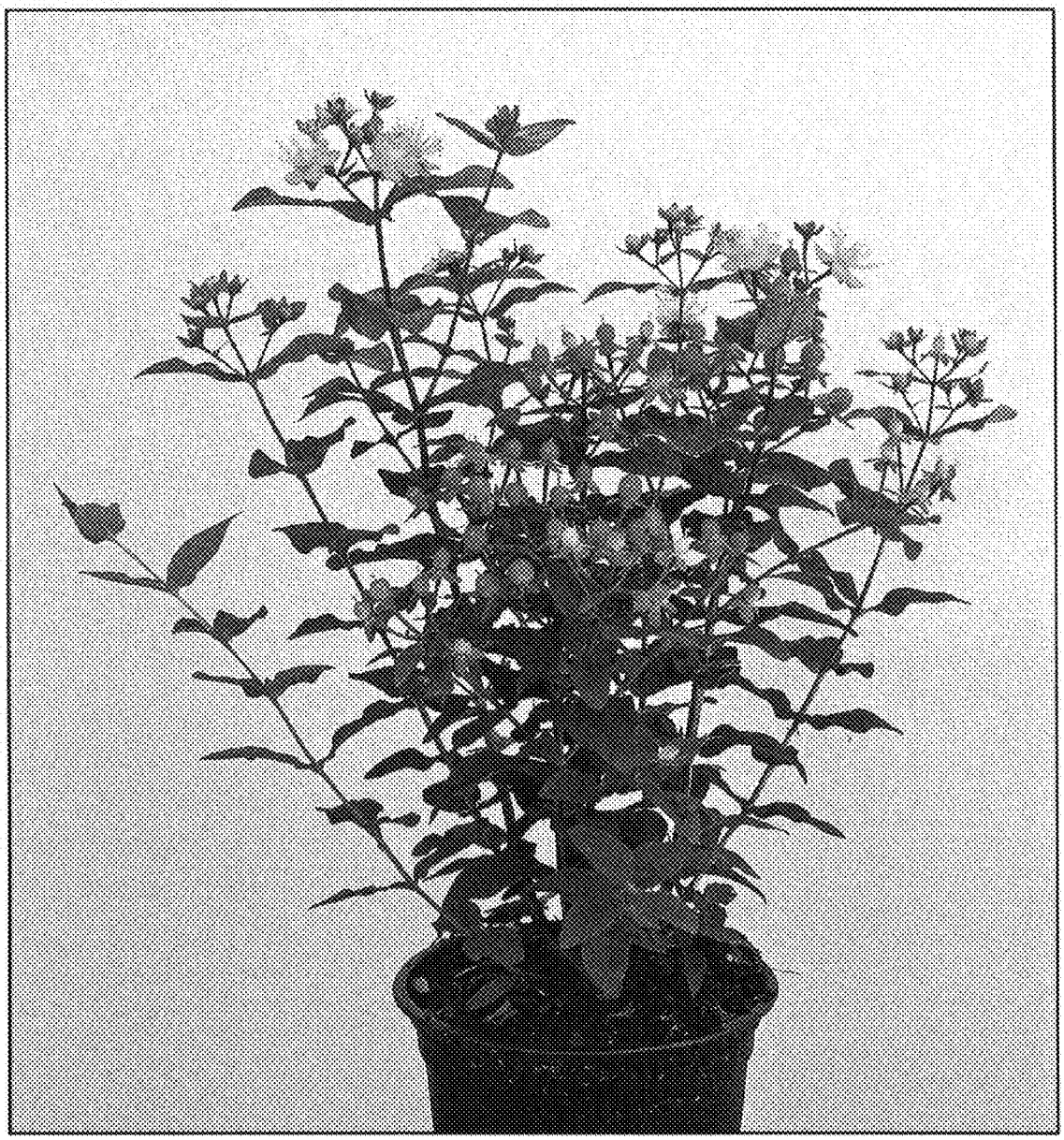

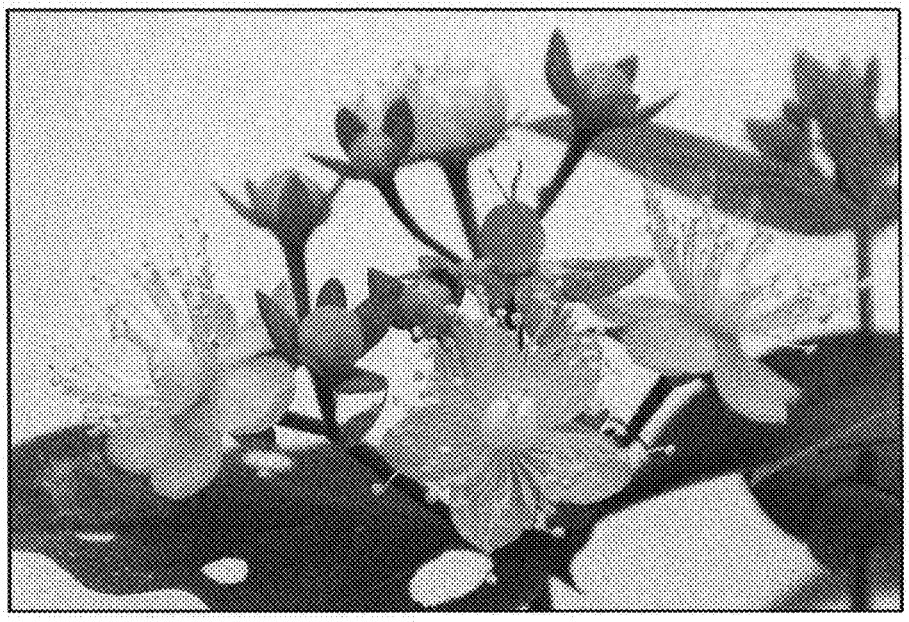
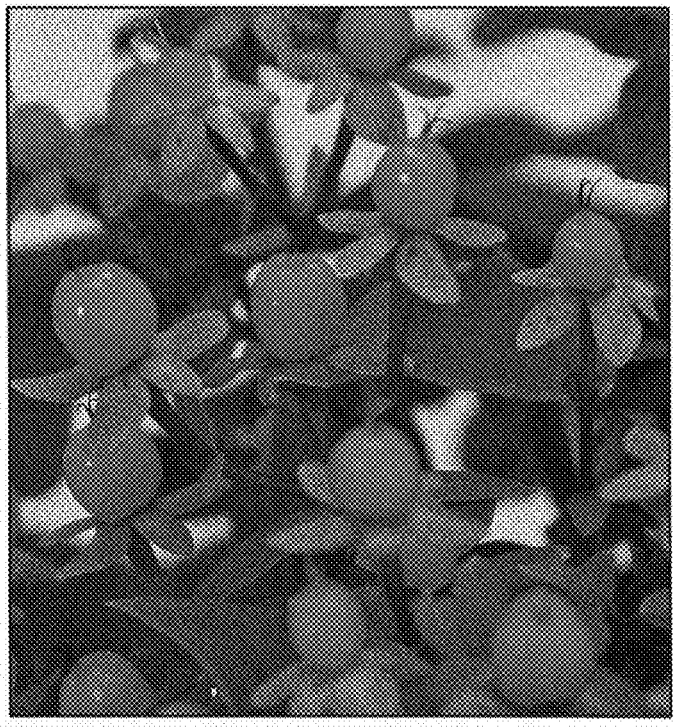
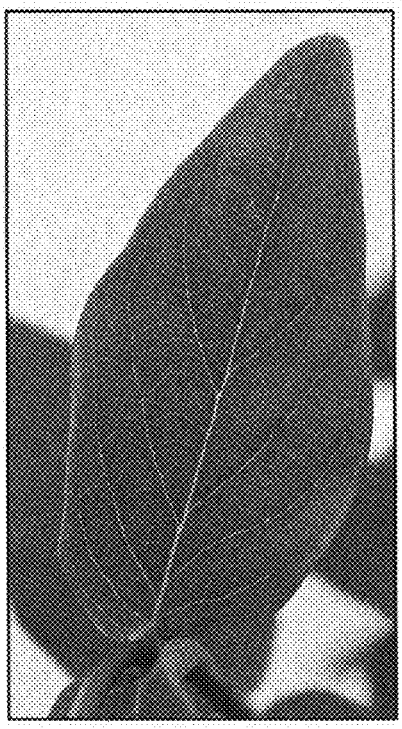

* * * * *